US008575221B2

(12) United States Patent
Masse et al.

(10) Patent No.: US 8,575,221 B2
(45) Date of Patent: Nov. 5, 2013

(54) DERIVATIVES OF DIMETHYLCURCUMIN

(75) Inventors: Craig E. Masse, Cambridge, MA (US); Roger D. Tung, Lexington, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 154 days.

(21) Appl. No.: 13/049,481

(22) Filed: Mar. 16, 2011

(65) Prior Publication Data
US 2011/0257271 A1 Oct. 20, 2011

Related U.S. Application Data

(60) Provisional application No. 61/314,842, filed on Mar. 17, 2010.

(51) Int. Cl.
*A61K 31/12* (2006.01)
*C07C 49/00* (2006.01)

(52) U.S. Cl.
USPC .......................................... 514/679; 568/325

(58) Field of Classification Search
USPC .......................................... 514/679; 568/325
See application file for complete search history.

(56) References Cited

U.S. PATENT DOCUMENTS

| | | |
|---|---|---|
| 6,221,335 B1 | 4/2001 | Foster |
| 6,440,710 B1 | 8/2002 | Keinan et al. |
| 6,503,921 B2 | 1/2003 | Naicker et al. |
| 6,603,008 B1 | 8/2003 | Ando et al. |
| 7,517,990 B2 | 4/2009 | Ito et al. |
| 2007/0082929 A1 | 4/2007 | Gant et al. |
| 2007/0197695 A1 | 8/2007 | Potyen et al. |
| 2008/0103122 A1 | 5/2008 | Veltri |
| 2009/0035362 A1 | 2/2009 | Shih et al. |

FOREIGN PATENT DOCUMENTS

| | | |
|---|---|---|
| WO | WO 95/26325 A2 | 10/1995 |
| WO | WO 03/088927 | 10/2003 |
| WO | 2006044379 A2 | 4/2006 |
| WO | 2007/118651 A1 | 10/2007 |

OTHER PUBLICATIONS

Parveen et al. CAS: 133: 281645, 2000.*
International Search Report for related PCT Application No. PCT/US11/28631, Apr. 28, 2011, 5 PP.
Written Opinion for related PCT Application No. PCT/US11/28631, Apr. 28, 2011, 5 PP.
Baille, T. A., "The Use of Stable Isotopes in Pharmacological Research," Pharmacological Reviews, 33(2): 81-132 (1981).
Browne, T. R., "Stable Isotope Techniques in Early Drug Development: An Economic Evaluation," J. Clin. Pharmacol., 38: 213-220 (1998).
Cherrah, Y., et al., "Study of Deuterium Isotope Effects on Protein Binding by Gas Chromatography/Mass Spectrometry. Caffeine and Deuterated Isotopomers," Biomedical and Environmental Mass Spectrometry, 14: 653-657 (1987).
Dyck, L. E., et al., "Effects of Deuterium Substitution on the Catabolism of β-Phenylethylamine: An In Vivo Study," Journal of Neurochemistry, 46(2): 399-404 (1986).
Fisher, M.B. et al., "The Complexities Inherent in Attempts to Decrease Drug Clearance by Blocking Sites of CYP-Mediated Metabolism," Curr. Opin. Drug Discov. Devel., 9(1):101-109 (2006).
Foster, A. B., "Deuterium Isotope Effects in Studies of Drug Metabolism," Trends in Pharmacological Sciences, 5: 524-527 (1984).
Foster, A. B., "Deuterium Isotope Effects in the Metabolism of Drugs and Xenobiotics: Implications for Drug Design," Advances in Drug Research, 14: 1-40 (1985).
Gouyette, A., "Synthesis of Deuterium-labelled Elliptinium and its Use in Metabolic Studies," Biomedical and Environmental Mass Spectrometry, 15: 243-247 (1988).
Haskins, N.J., "The Application of Stable Isotopes in Biomedical Research," Biomedical Mass Spectrometry, 9(7): 269-277 (1982).
Hatcher, H., et al., "Curcumin: From Ancient Medicine to Current Clinical Trials," Cellular and Molecular Life Sciences, 1-22 (2008).
Honma, S., et al., "The Metabolism of Roxatidine Acetate Hydrochloride," Drug Metabolism and Disposition, 15(4): 551-559 (1987).
Ireson, C.R., et al., "Metabolism of the Cancer Chemopreventive Agent Curcumin in Human and Rat Intestine," Cancer Epidemiology, Biomarkers and Prevention, 11: 105-111 (Jan. 2002).
Kushner, D.J. et al., "Pharmacological Uses and Perspectives of Heavy Water and Deuterated Compounds," Can. J. Physiol. Pharmacol., 77:79-88 (1999).
Parveen, I., et al., "Labeled Compounds of Interest as Antitumor Agents-VII. [$^2$H] and [$^{14}$C]-Curcumin", Journal of Labelled Compounds and Radiopharmaceuticals, 43(9): 883-339 (2000).
Pieniaszek, H. J., et al., "Moricizine Bioavailability via Simultaneous, Dual, Stable Isotope Administration: Bioequivalence Implications," J. Clin. Pharmacol, 39: 817-825 (1999).

(Continued)

*Primary Examiner* — Rei-tsang Shiao
(74) *Attorney, Agent, or Firm* — McCarter & English, LLP; Steven G. Davis

(57) ABSTRACT

The invention relates to compounds of Formula I or Ia as disclosed herein:

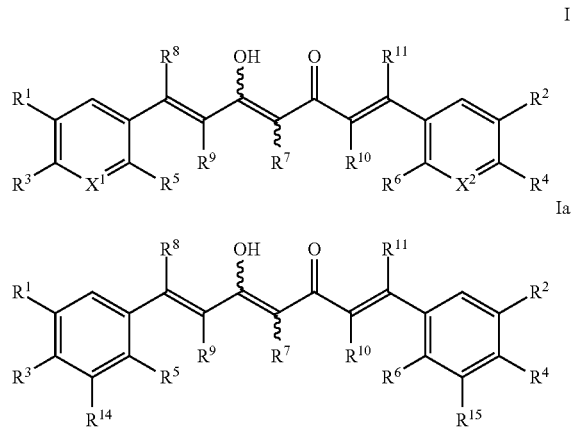

or pharmaceutically acceptable salts thereof or tautomers thereof.

18 Claims, No Drawings

(56) References Cited

OTHER PUBLICATIONS

Tamvakopoulos, C., et al., "Analysis of the In Vitro metabolites of Diferuloylmethane (Curcumin) by Liquid Chromatography-Tandem Mass Spectrometry," European Journal of Drug Metabolism and Pharmacokinetics, 32(1): 51-57 (2007).

Tamvakopoulos, C., et al., "Metabolism and Anticancer Activity of the Curcumin Analogue, Dimethoxycurcumin," Clin. Cancer Res., 13(4): 1269-1277 (2007).

Tonn, G. R., et al., "Simultaneous Analysis of Diphenhydramine and a Stable Isotope Analog ($^2H_{10}$) Diphenhydramine Using Capillary Gas Chromatography with Mass Selective Detection in Biological Fluids from Chronically Instrumented Pregnant Ewes," Biological Mass Spectrometry, 22: 633-642 (1993).

Wolen, R. L., "The Application of Stable Isotopes to Studies of Drug Bioavailability and Bioequivalence," J. Clin. Pharmacol., 26: 419-424 (1986).

\* cited by examiner

DERIVATIVES OF DIMETHYLCURCUMIN

CROSS-REFERENCE TO RELATED APPLICATIONS

This application claims priority under 35 U.S.C. §119(e) to U.S. Provisional Application No. 61/314,842, filed Mar. 17, 2010, which is incorporated by reference herein in its entirety.

BACKGROUND OF THE INVENTION

Many current medicines suffer from poor absorption, distribution, metabolism and/or excretion (ADME) properties that prevent their wider use. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56(6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, A B, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

This invention relates to novel derivatives of curcumin and dimethylcurcumin and pharmaceutically acceptable salts thereof. This invention also provides compositions comprising a compound of this invention and the use of such compositions in methods of treating diseases and conditions that are beneficially treated by administering curcumin or dimethylcurcumin.

Curcuminoids such as dimethylcurcumin are capable of acting as androgen receptor antagonists. Such compounds may be useful for the treatment of androgen-related afflictions including baldness, hirsutism, behavioral disorders, acne, alopecia, skin lesions, Kennedy's disease or spinobulbar muscular atrophy and spermatogenesis where inhibition of spermatogenesis is desired. Additionally, the compounds may be useful for treatment of psoriasis, Alzheimer's disease, mild cognitive impairment, asthma, type 2 diabetes, optic neuropathy, rheumatoid arthritis, osteoarthritis, major depressive disorder, kidney allografts, oral lichen planus, irritable bowel syndrome (IBS), ulcerative colitis, Crohn's disease, chemoradiation side effects including but not limited to radiation induced dermatitis and chemotherapy induced mucositis and cancer including, but not limited to, multiple myeloma, pancreatic cancer, myleodysplastic syndromes, colon cancer, colorectal cancer, skin cancer, small cell lung cancer, testicular cancer, lymphoma, leukemia, esophageal cancer, stomach cancer, breast cancer, endometrial cancer, ovarian cancer, central nervous system cancer, liver cancer, prostate cancer, familial adenomatous polyposis (FAP), uterine cervical dysplasia, cutaneous T-cell lymphoma, head and neck cancer and osteosarcoma.

Dimethylcurcumin is currently undergoing clinical trial evaluation for use in topical treatment of acne and alopecia. Preclinical studies are also underway for the treatment of skin lesions and Kennedy's disease or spinobulbar muscular atrophy. Curcumin is currently undergoing clinical trial evaluation for use in treatment of asthma, type 2 diabetes, Alzheimer's disease, mild cognitive impairment, optic neuropathy, rheumatoid arthritis, osteoarthritis, major depressive disorder, kidney allografts, psoriasis, oral lichen planus, multiple myeloma, myelodysplastic syndrome, colorectal cancer, familial adenomatous polyposis (FAP), uterine cervical dysplasia, cutaneous T-cell lymphoma, head and neck cancer, pancreatic cancer, osteosarcoma, irritable bowel syndrome (IBS), ulcerative colitis, Crohn's disease, chemoradiation side effects including but not limited to radiation induced dermatitis and chemotherapy induced mucositis.

Despite the beneficial activities of dimethylcurcumin, there is a continuing need for compositions or derivatives thereof that provide the beneficial effects of dimethylcurcumin, but reduce or avoid the adverse side effects.

DEFINITIONS

The term "treat" means decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

The term "alkyl" refers to a monovalent saturated hydrocarbon group. A $C_1$-$C_6$ alkyl is an alkyl having from 1 to 6 carbon atoms. An alkyl may be linear or branched. Examples of alkyl groups include methyl; ethyl; propyl, including n-propyl and isopropyl; butyl, including n-butyl, isobutyl, sec-butyl, and t-butyl; pentyl, including, for example, n-pentyl, isopentyl, and neopentyl; and hexyl, including, for example, n-hexyl and 2-methylpentyl.

The term "alkenyl" refers to a monovalent saturated hydrocarbon group having one or more double bonds. A $C_2$-$C_6$ alkenyl is an alkenyl having from 2 to 6 carbon atoms. An alkenyl may be linear or branched. Examples of alkenyl groups include $CH_2=CH-$; $CH_3-CH=CH-$; $-CH_2-CH=CH_2-$; $(CH_3)_2C=CH-$; $CH_2=C(CH_3)-CH_2-$; and $(CH_3)_2CH-CH=CH-$.

It will be recognized that some variation of natural isotopic abundance occurs in a synthesized compound depending upon the origin of chemical materials used in the synthesis. Thus, a preparation of dimethylcurcumin will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5° A of the compound.

The invention also provides salts of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, O-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert" and "t-" each refer to tertiary. "US" refers to the United States of America.

The term "substituted with deuterium" means that one or more hydrogen atoms in the indicated moiety are substituted with a deuterium atom.

Therapeutic Compounds

The present invention provides a compound of Formula I:

I or a pharmaceutically acceptable salt thereof or a tautomer thereof,
wherein:

$R^1$, $R^2$, $R^3$ and $R^4$ are each independently selected from the group consisting of —OH, —O($C_1$-$C_6$ alkyl), —$NO_2$, —$NH_2$, —NH($C_1$-$C_6$ alkyl) and —N($C_1$-$C_6$ alkyl)$_2$, wherein each $C_1$-$C_6$ alkyl is optionally and independently substituted with one or more deuterium;

$R^5$ and $R^6$ are each independently hydrogen, deuterium, halo, or —$NO_2$;

$R^7$ is hydrogen, deuterium, or —$R^{13}$;

$R^{13}$ is ($C_2$-$C_6$) alkenyl optionally substituted with one or more deuterium and substituted with —C(O)$R^{12}$;

$R^{12}$ is —$OCH_3$, —$OCH_2CH_3$, —$NH(CH_2CH_3)$, —CN, or —$CH_2OH$, wherein each of —$OCH_3$, —$OCH_2CH_3$, —NH($CH_2CH_3$), and —$CH_2OH$ is optionally substituted with one or more deuterium;

$R^8$ and $R^{11}$ are each independently hydrogen or deuterium;
$R^9$ and $R^{10}$ are each independently hydrogen or deuterium;
$X^1$ and $X^2$ are each independently N, CH, CD, C($OCH_3$), C($OCD_3$) or C($NO_2$);
provided that at least one of $R^1$, $R^2$, $R^3$, $R^4$, $R^5$, $R^6$, $R^7$, $R^8$, $R^{11}$, $R^9$, $R^{10}$, $X^1$ and $X^2$ comprises deuterium;
and provided that the compound of Formula I is not In one embodiment of the invention, $R^1$, $R^2$, $R^3$, and $R^4$ are independently selected from —OH, —$OCH_3$, and —$OCD_3$.

In one embodiment, $R^5$ and $R^6$ are each hydrogen or each deuterium.

In one embodiment, $R^7$ is hydrogen or deuterium.
In one embodiment, $X^1$ is CH or CD.
In one embodiment, $X^2$ is CH or CD.
In one embodiment, $R^7$ is $R^{13}$, wherein $R^{13}$ is ($C_2$-$C_6$) alkenyl optionally substituted with one or more deuterium and with —C(O)$R^{12}$, and $R^{12}$ is —$OCD_3$, —$OCD_2CD_3$, —N(H)$CD_2CD_3$, or —$CD_2OH$.

Examples of compounds of Formula I wherein $X^1$=$X^2$=CH and $R^5$=$R^6$=H include the following compounds or pharmaceutically acceptable salts thereof or tautomers thereof, wherein any atom not designated as deuterium is present at its natural isotopic abundance:

TABLE 1

Examples of Compounds of Formula I wherein $X^1$=$X^2$=CH and $R^5$=$R^6$=H

| Compound | $R^1$ | $R^2$ | $R^3$ | $R^4$ | $R^7$ | $R^8$ | $R^9$ | $R^{10}$ | $R^{11}$ |
|---|---|---|---|---|---|---|---|---|---|
| 100 | $OCD_3$ | $OCD_3$ | OH | $OCD_3$ | D | D | D | D | D |
| 101 | $OCD_3$ | $OCD_3$ | OH | $OCD_3$ | H | D | D | D | D |
| 102 | $OCD_3$ | $OCD_3$ | OH | $OCD_3$ | H | H | D | D | D |
| 103 | $OCD_3$ | $OCD_3$ | OH | $OCD_3$ | H | D | D | D | H |
| 104 | $OCD_3$ | $OCD_3$ | OH | $OCD_3$ | H | H | D | D | H |
| 105 | $OCD_3$ | $OCD_3$ | OH | $OCD_3$ | H | H | H | H | H |
| 106 | $OCD_3$ | $OCD_3$ | OH | $OCD_3$ | H | D | H | H | D |
| 107 | $OCD_3$ | $OCD_3$ | OH | $OCD_3$ | H | D | H | H | H |
| 108 | $OCD_3$ | $OCD_3$ | OH | $OCD_3$ | H | H | H | H | D |
| 109 | $OCH_3$ | $OCD_3$ | OH | $OCD_3$ | D | D | D | D | D |
| 110 | $OCH_3$ | $OCD_3$ | OH | $OCD_3$ | H | D | D | D | D |
| 111 | $OCH_3$ | $OCD_3$ | OH | $OCD_3$ | H | H | D | D | D |
| 112 | $OCH_3$ | $OCD_3$ | OH | $OCD_3$ | H | D | D | D | H |
| 113 | $OCH_3$ | $OCD_3$ | OH | $OCD_3$ | H | H | D | D | H |
| 114 | $OCH_3$ | $OCD_3$ | OH | $OCD_3$ | H | H | H | H | H |
| 115 | $OCH_3$ | $OCD_3$ | OH | $OCD_3$ | H | D | H | H | D |

TABLE 1-continued

Examples of Compounds of Formula I wherein
$X^1=X^2=CH$ and $R^5=R^6=H$

| Compound | $R^1$ | $R^2$ | $R^3$ | $R^4$ | $R^7$ | $R^8$ | $R^9$ | $R^{10}$ | $R^{11}$ |
|---|---|---|---|---|---|---|---|---|---|
| 116 | OCH₃ | OCD₃ | OH | OCD₃ | H | D | H | H | H |
| 117 | OCH₃ | OCD₃ | OH | OCD₃ | H | H | H | H | D |
| 118 | OCD₃ | OCH₃ | OH | OCH₃ | D | D | D | D | D |
| 119 | OCD₃ | OCH₃ | OH | OCH₃ | H | D | D | D | D |
| 120 | OCD₃ | OCH₃ | OH | OCH₃ | H | H | D | D | D |
| 121 | OCD₃ | OCH₃ | OH | OCH₃ | H | D | D | D | H |
| 122 | OCD₃ | OCH₃ | OH | OCH₃ | H | H | D | H | H |
| 123 | OCD₃ | OCH₃ | OH | OCH₃ | H | H | H | H | H |
| 124 | OCD₃ | OCH₃ | OH | OCH₃ | H | D | H | H | D |
| 125 | OCD₃ | OCH₃ | OH | OCH₃ | H | D | H | H | H |
| 126 | OCD₃ | OCH₃ | OH | OCH₃ | H | H | H | H | D |
| 127 | OCH₃ | OCH₃ | OH | OCH₃ | D | D | D | D | D |
| 128 | OCH₃ | OCH₃ | OH | OCH₃ | H | D | D | D | D |
| 129 | OCH₃ | OCH₃ | OH | OCH₃ | H | H | D | D | D |
| 130 | OCH₃ | OCH₃ | OH | OCH₃ | H | D | D | D | H |
| 131 | OCH₃ | OCH₃ | OH | OCH₃ | H | H | D | H | H |
| 132 | OCH₃ | OCH₃ | OH | OCH₃ | H | D | H | H | D |
| 133 | OCH₃ | OCH₃ | OH | OCH₃ | H | D | H | H | H |
| 134 | OCH₃ | OCH₃ | OH | OCH₃ | H | H | H | H | D |

In one embodiment, the compound is compound 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 133 or 134 in Table 1, or a pharmaceutically acceptable salt thereof or a tautomer thereof.

In one embodiment, the compound of Formula I is a compound of Formula Ia:

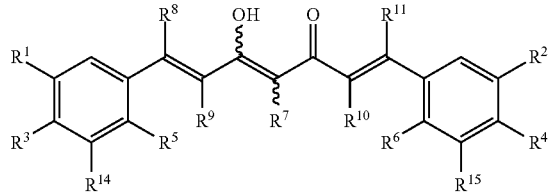

Ia or a pharmaceutically acceptable salt thereof or a tautomer thereof,
wherein:

$R^1$ and $R^2$ are the same and are selected from the group consisting of —OH, —O(C₁-C₆ alkyl), —NO₂, —NH₂, —NH(C₁-C₆ alkyl) and —N(C₁-C₆ alkyl)₂, wherein each C₁-C₆ alkyl is optionally and independently substituted with one or more deuterium;

$R^3$ and $R^4$ are the same and are selected from the group consisting of —OH, —O(C₁-C₆ alkyl), —NO₂, —NH₂, —NH(C₁-C₆ alkyl) and —N(C₁-C₆ alkyl)₂, wherein each C₁-C₆ alkyl is optionally and independently substituted with one or more deuterium;

$R^5$ and $R^6$ are the same and are selected from the group consisting of hydrogen and deuterium;

$R^7$ is selected from hydrogen and deuterium;

$R^9$ and $R^{10}$ are the same and are selected from hydrogen and deuterium;

$R^8$ and $R^{11}$ are the same and are selected from hydrogen and deuterium;

$R^{14}$ and $R^{15}$ are the same and are selected from hydrogen and deuterium;

provided that at least one of $R^1$, $R^2$, $R^3$, $R^4$, $R^5$, $R^6$, $R^7$, $R^8$, $R^{11}$, $R^9$, $R^{10}$, $R^{14}$ and $R^{15}$ comprises deuterium;

and provided that the compound of Formula Ia is not

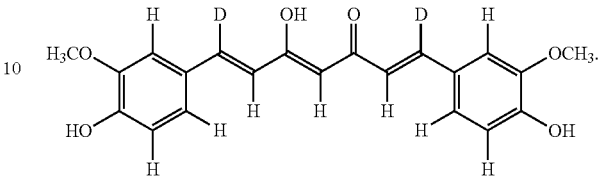

In one embodiment of the compound of Formula Ia, $R^7$, $R^9$ and $R^{10}$ are the same and are selected from hydrogen and deuterium.

In another embodiment of the compound of Formula Ia, $R^1$ and $R^2$ are the same and are selected from —OH, $R^1$ and $R^2$ are both —OCH₃ and —OCD₃; and $R^3$ and $R^4$ are the same and are selected from —OH, —OCH₃ and —OCD₃. Alternatively, —OCH₃ and —OCD₃; and $R^3$ and $R^4$ are both —OH.

In another set of embodiments of Formula I or Ia, any atom not designated as deuterium in any of the embodiments set forth above is present at its natural isotopic abundance.

Examples of compounds of Formula Ia, wherein $R^5=R^6=H$, and $R^{14}=R^{15}=H$, are the following compounds or pharmaceutically acceptable salts thereof or tautomers thereof, wherein any atom not designated as deuterium is present at its natural isotopic abundance:

TABLE 2

Example of Compounds of Formula Ia

| Compound | $R^1=R^2$ | $R^3=R^4$ | $R^7$ | $R^8=R^{11}$ | $R^9=R^{10}$ |
|---|---|---|---|---|---|
| 200 | OCD₃ | OCD₃ | D | D | D |
| 201 | OCD₃ | OCH₃ | D | D | D |
| 202 | OCH₃ | OCD₃ | D | D | D |
| 203 | OCH₃ | OCH₃ | D | D | D |
| 204 | OCD₃ | OCD₃ | D | H | D |
| 205 | OCD₃ | OCD₃ | H | D | H |
| 206 | OCD₃ | OCH₃ | D | H | D |
| 207 | OCD₃ | OCH₃ | H | D | H |
| 208 | OCH₃ | OCD₃ | D | H | D |
| 209 | OCH₃ | OCD₃ | H | D | H |
| 210 | OCH₃ | OCH₃ | D | H | D |
| 211 | OCH₃ | OCH₃ | H | D | H |
| 212 | OCD₃ | OCD₃ | H | H | H |
| 213 | OCD₃ | OCH₃ | H | H | H |
| 214 | OCH₃ | OCD₃ | H | H | H |
| 215 | OCD₃ | OCD₃ | H | D | D |
| 216 | OCD₃ | OCH₃ | H | D | D |
| 217 | OCH₃ | OCD₃ | H | D | D |
| 218 | OCH₃ | OCH₃ | H | D | D |
| 219 | OCD₃ | OCD₃ | H | H | D |
| 220 | OCD₃ | OCH₃ | H | H | D |
| 221 | OCH₃ | OCD₃ | H | H | D |
| 222 | OCH₃ | OCH₃ | H | H | D |

In one embodiment, the compound is compound 200, 201, 202, 203, 204, 205, 206, 207, 208, 209, 210, 212, 213, 214, 215, 216, 217, 218, 219, 220, 221 or 222 in Table 2, or a pharmaceutically acceptable salt thereof or a tautomer thereof.

Additional examples of compounds of Formula Ia, wherein $R^5=R^6=H$, and $R^{14}=R^{15}=H$, are the following compounds or pharmaceutically acceptable salts thereof or tautomers thereof, wherein any atom not designated as deuterium is present at its natural isotopic abundance:

TABLE 3

Example of Compounds of Formula Ia

| Compound | $R^1=R^2$ | $R^3=R^4$ | $R^7$ | $R^8=R^{11}$ | $R^9=R^{10}$ |
|---|---|---|---|---|---|
| 300 | OCD$_3$ | OH | D | D | D |
| 301 | OCH$_3$ | OH | D | D | D |
| 302 | OCD$_3$ | OH | D | H | D |
| 303 | OCD$_3$ | OH | H | D | H |
| 304 | OCH$_3$ | OH | D | H | D |
| 306 | OCD$_3$ | OH | H | H | H |
| 307 | OCD$_3$ | OH | H | D | D |
| 308 | OCH$_3$ | OH | H | D | D |
| 309 | OCD$_3$ | OH | H | H | D |
| 310 | OCH$_3$ | OH | H | H | D |

In one embodiment, the compound is compound 300, 301, 302, 303, 304, 306, 307, 308, 309 or 310 in Table 3, or a pharmaceutically acceptable salt thereof or a tautomer thereof.

With reference to the geometry of the enolic double bond in the compounds of Formula I and Ia, that is, the double bond shown as

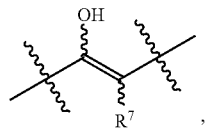

the structures in each case have (E) stereochemistry or (Z) stereochemistry, or exist as a mixture of the two stereoisomers. The above stereoisomers or mixtures thereof are all encompassed by the invention.

The invention encompasses tautomers of the compounds of Formula I and Ia. With reference to the compound of Formula I, examples of tautomers include I-1 and I-2, shown below:

I-1

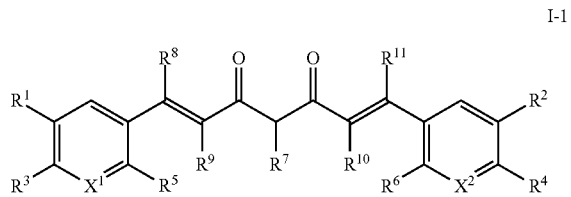

I-2

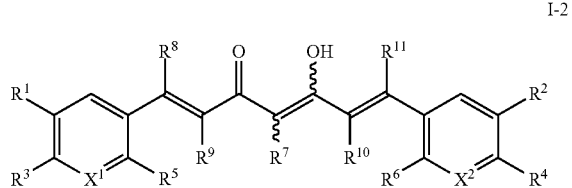

With reference to the compound of Formula Ia, examples of tautomers include Ia-1 and Ia-2, shown below:

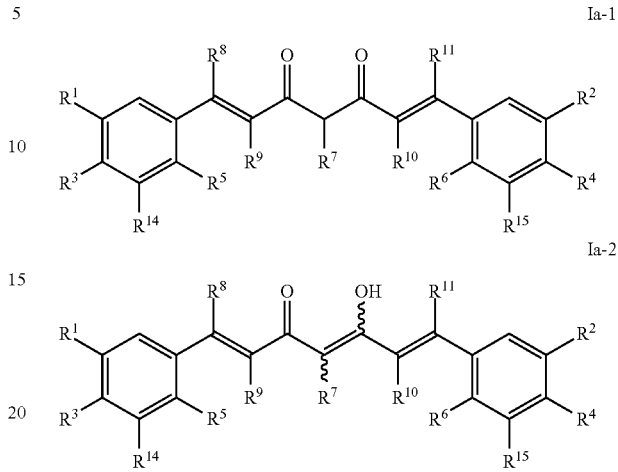

With reference to the geometry of the enolic double bond in Formula I-2 and Ia-2, that is, the double bond shown as

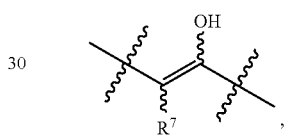

the structures in each case have (E) stereochemistry or (Z) stereochemistry, or exist as a mixture of the two stereoisomers. The above stereoisomers or mixtures thereof are all encompassed by the invention.

Structures I-1 and Ia-1 at the carbon bonded to $R^7$ have (R) stereochemistry or (S) stereochemistry, or exist as a mixture of the two stereoisomers. The above stereoisomers or mixtures thereof are all encompassed by the invention.

The synthesis of compounds of Formula I and Formula Ia may be readily achieved by synthetic chemists of ordinary skill by reference to the Exemplary Synthesis and Examples disclosed herein. Relevant procedures analogous to those of use for the preparation of compounds of Formula I and Formula Ia and intermediates thereof are disclosed, for instance in Lee, K H et al, Bioorg Med Chem, 2006, 14: 2527; Lee, K H et al, J Med Chem, 2006, 49: 3963; Threadgill, M D et al, J Label Comp Radiopharm, 2000, 43: 883; and Lee, K H et al, WO 03/088927 A2.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

Compounds of Formula I and Formula Ia can be prepared by a person skilled in the art using appropriately deuterated reagents and/or intermediates according to the general procedures shown in Schemes 1-3.

Scheme 1(a): Synthesis of Compounds of Formula Ia Wherein $R^1 = R^2$, $R^3 = R^4$, $R^5 = R^6$ and $R^8 = R^{11}$.

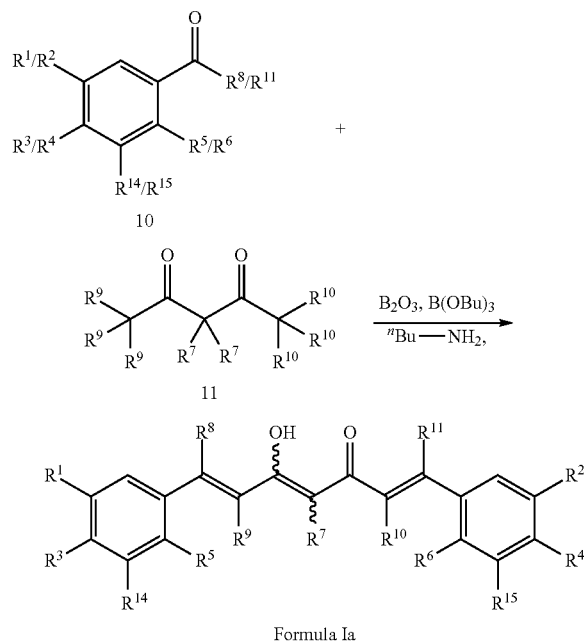

A convenient method for synthesizing compounds of Formula Ia, wherein $R^1=R^2$, $R^3=R^4$, $R^5=R^6$ and $R^8=R^{11}$ is depicted in Scheme 1(a). Treatment of the appropriately deuterated 3,4-dialkoxybenzaldehyde 10 (2 equivalents) with an appropriately deuterated 2,4-pentandione 11 having $R^9=R^{10}$ in the presence of boric anhydride, tributyl borate, and n-butylamine under thermal conditions in a manner analogous to that described by Lee, K. H. et al., Bioorganic and Medicinal Chemistry, 2006, 14: 2527-2534 affords compounds of Formula Ia.

Scheme 1(b): Synthesis of Compounds of Formula I.

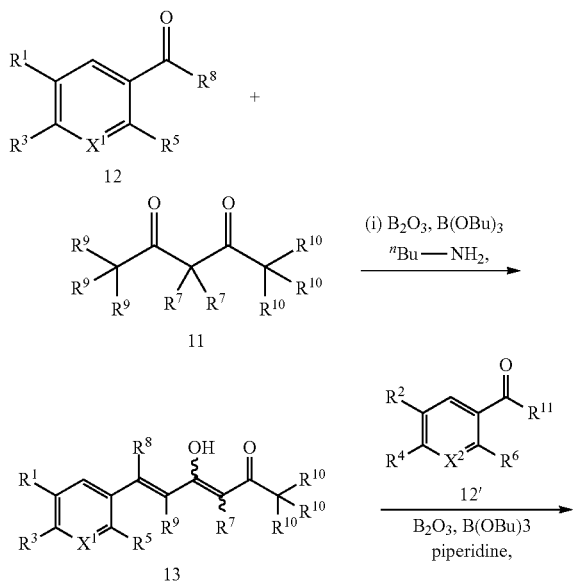

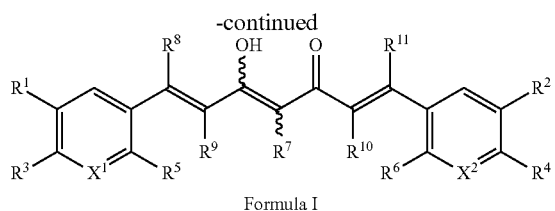

Treatment of the appropriately deuterated starting material 12 with excess 11 (wherein) $R^9=R^{10}$ as described above in Scheme 1(a) and in a manner analogous to that described by Lee, K H et al, J Med Chem, 2006, 49: 3963, affords intermediate 13 which upon treatment with one equivalent of a different appropriately deuterated 12', affords compounds of Formula I wherein $R^9=R^{10}$. As an example in Scheme 1b), $X^1$ and $X^2$ are each independently CH or CD and $R^5$ and $R^6$ are each independently hydrogen or deuterium.

Conversely, 2 equivalents of starting material 12 may be treated with 1 equivalent of an appropriately deuterated intermediate 11 as described in Scheme 1(a) having $R^9$ the same as $R^{10}$ or different from $R^{10}$ to yield compounds of Formula I wherein $R^1=R^2$, $R^3=R^4$, $R^5=R^6$, $R^8=R^{11}$ and $X^1=X^2$.

Scheme 2: Synthesis of Various Deuterated Forms of Intermediate 10.

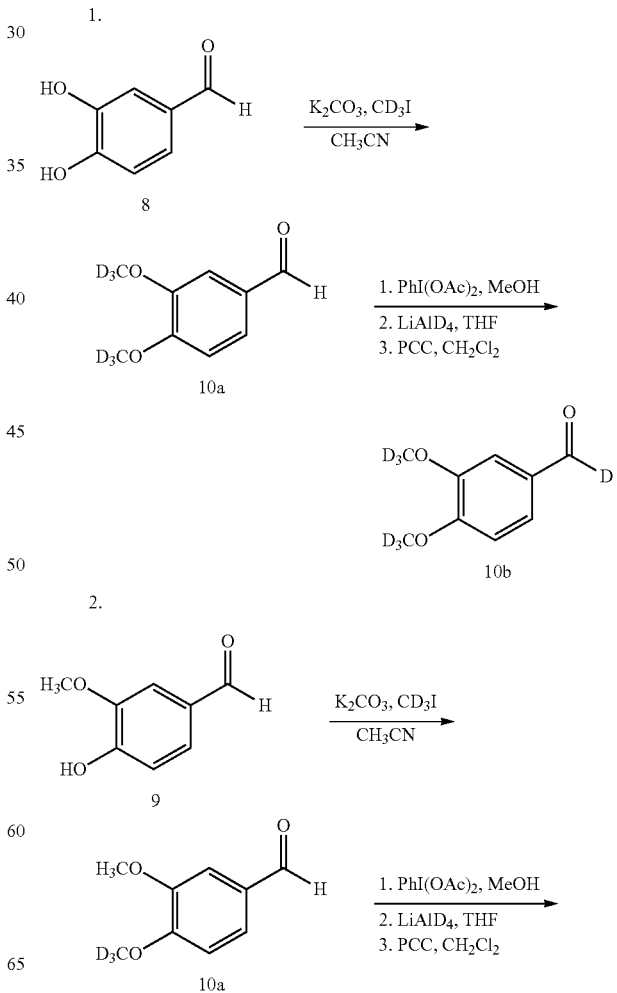

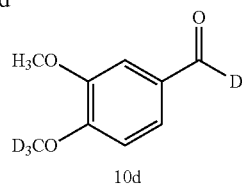
10d

A method for the synthesis of appropriately deuterated 3,4-dialkoxybenzaldehyde derivatives 10a-10d is shown in Scheme 2. Treatment of commercially available 3,4-dihydroxybenzaldehyde (8) or vanillin (9) with commercially available iodomethane-d3 in the presence of potassium carbonate in a manner analogous to that described by Chem, J. W. et al., Journal of Organic Chemistry, 2002, 67: 6772-6787 affords 3,4-bis(trideuteromethoxy)benzaldehyde (10a) or 3-methoxy-4-(trideuteromethoxy)benzaldehyde (10c), respectively. Oxidation of deuterated benzaldehydes 10a and 10c with (diacetoxyiodo)benzene in methanol using a procedure analogous to that described by Karade, N. N. et al., Journal of Chemical Research, 2005: 274-276 gives the corresponding deuterated methyl-benzoates. Reduction of the respective deuterated methyl-benzoates with lithium aluminum deuteride followed by subsequent oxidation of the corresponding benzylic alcohols with pyridinium chlorochromate (PCC) using a procedure analogous to that described by Luzzio, F. A. et al., Journal of Organic Chemistry, 1989, 54: 5387-5390 affords benzaldehydes 10b and 10d, respectively. Likewise, intermediates 12 and 12', wherein $X^1$ and $X^2$ are each independently CH, CD, C(OCH$_3$), C(OCD$_3$) or C(NO$_2$), may be prepared as described above starting with the appropriately substituted 3,4-dihydroxybenzaldehyde in place of starting compound 8. These intermediates are of use for the preparation of compounds of Formula I as outlined in Scheme 1b.

Scheme 3a: Synthesis of Intermediates 11b and 11c.

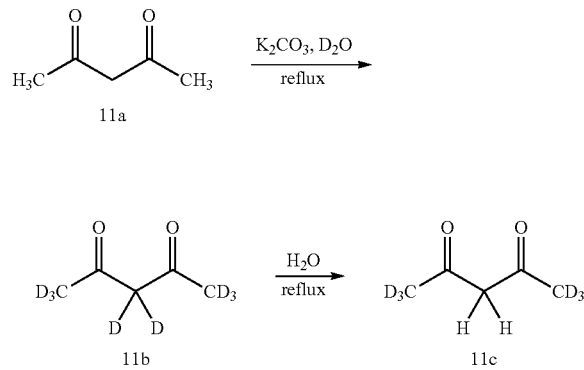

One approach to the synthesis of deuterated 2,4-pentandione 11b is shown in Scheme 3a, Commercially available 2,4-pentandione (11a) is treated with deuterated water in the presence of potassium carbonate under conditions of reflux according to the procedure described by Elguero, J. et al., Journal of Labelled Compounds and Radiopharmaceuticals, 1990, 28: 967-970 to give the desired perdeuterated 2,4-pentanedione 11b. Treatment of 11b with water under conditions of reflux would allow the proton deuterium exchange at the 3-position to yield intermediate 11c.

Scheme 3b: Synthesis of Intermediate 11d.

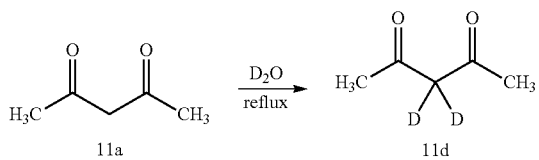

Intermediate 11d may be prepared as shown in Scheme 3b and as described by Ito, Y. et al., Bulletin of the Chemical Society of Japan, 1981, 54(1): 150-8. Commercially available 2,4-pentandione (11a) stirred under reflux in the presence of deuterium oxide affords 3-d$_2$-2,4-pentandione (11d).

Scheme 3c: Synthesis of Intermediates 11e and 11f.

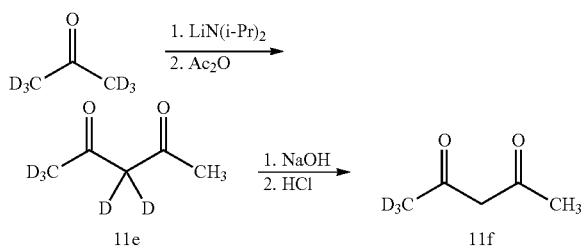

Intermediate 11f may be prepared as shown in Scheme 3c and as described by Challacombe, K. et al., Journal of the Chemical Society, Perkin Transactions 1: Organic and Bio-Organic Chemistry (1972-1999); 1988, (8): 2213-18. Treatment of commercially available acetone-d$_6$ with lithium diisopropylamide followed by acetic anhydride affords intermediate 11e which when treated with NaOH followed by affords 1-d$_3$-2,4-pentandione (11f).

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Additional methods of synthesizing compounds of Formula I or Ia and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene, T W et al., *Protective Groups in Organic Synthesis*, 3$^{rd}$ Ed., John Wiley and Sons (1999); Fieser, L et al., Fieser and *Fieser's Reagents for Organic Synthesis*, John Wiley and Sons (1994); and Paquette, L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free pharmaceutical compositions comprising an effective amount of a compound of Formula I (including any of the formulae herein), or a pharmaceutically acceptable salt thereof or a tautomer thereof; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the subject, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as curcumin or dimethylcurcumin. Such agents include other androgen receptor antagonists.

Preferably, the second therapeutic agent is an agent useful in the treatment of a disease or condition selected from baldness, hirsutism, behavioral disorders, acne, alopecia, skin lesions, Kennedy's disease or spinobulbar muscular atrophy and spermatogenesis where inhibition of spermatogenesis is desired, psoriasis, Alzheimer's disease, mild cognitive impairment, asthma, type 2 diabetes, optic neuropathy, rheumatoid arthritis, osteoarthritis, major depressive disorder, kidney allografts, oral lichen planus, irritable bowel syndrome (IBS), ulcerative colitis, Crohn's disease, chemoradiation side effects including but not limited to radiation induced dermatitis and chemotherapy induced mucositis and cancer including, but not limited to, multiple myeloma, pancreatic cancer, myleodysplastic syndromes, colon cancer, colorectal cancer, skin cancer, small cell lung cancer, testicular cancer, lymphoma, leukemia, esophageal cancer, stomach cancer, breast cancer, endometrial cancer, ovarian cancer, central nervous system cancer, liver cancer, prostate cancer, familial adenomatous polyposis (FAP), uterine cervical dysplasia, cutaneous T-cell lymphoma, head and neck cancer and osteosarcoma.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat the target disorder.

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In one embodiment, an effective amount of a compound of this invention can range from 50 mg to 2,000 mg/dose with a dosing of one to three times per day.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician. For example, guidance for selecting an effective dose can be determined by reference to the prescribing information for niacin.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In one embodiment, the invention provides a method of treating a disease that is beneficially treated by dimethylcurcumin or curcumin in a subject in need thereof, comprising the step of administering to the subject an effective amount of a compound of Formula I or Ia or a pharmaceutically acceptable salt thereof or a tautomer thereof, or a composition of this invention. Such diseases are well known in the art and include—baldness, hirsutism, behavioral disorders, acne, alopecia, skin lesions, Kennedy's disease or spinobulbar muscular atrophy and spermatogenesis where inhibition of spermatogenesis is desired, psoriasis, Alzheimer's disease, mild cognitive impairment, asthma, type 2 diabetes, optic neuropathy, rheumatoid arthritis, osteoarthritis, major depressive disorder, kidney allografts, oral lichen planus, irritable bowel syndrome (IBS), ulcerative colitis, Crohn's disease, chemoradiation side effects including but not limited to radiation induced dermatitis and chemotherapy induced mucositis and cancer including, but not limited to, multiple myeloma, pancreatic cancer, myleodysplastic syndromes, colon cancer, colorectal cancer, skin cancer, small cell lung cancer, testicular cancer, lymphoma, leukemia, esophageal cancer, stomach cancer, breast cancer, endometrial cancer, ovarian cancer, central nervous system cancer, liver cancer, prostate cancer, familial adenomatous polyposis (FAP), uterine cervical dysplasia, cutaneous T-cell lymphoma, head and neck cancer and osteosarcoma.

In one particular embodiment, the method of this invention is used to treat a disease or condition selected from acne, alopecia, skin lesions and Kennedy's disease or spinobulbar muscular atrophy.

In one particular embodiment, the method of this invention is used to treat a disease or condition selected from multiple myeloma, pancreatic cancer, myleodysplastic syndromes, colon cancer, colorectal cancer, skin cancer, small cell lung cancer, testicular cancer, lymphoma, leukemia, esophageal cancer, stomach cancer, breast cancer, endometrial cancer, ovarian cancer, central nervous system cancer, liver cancer, prostate cancer, familial adenomatous polyposis (FAP), uterine cervical dysplasia, cutaneous T-cell lymphoma, head and neck cancer and osteosarcoma.

In one particular embodiment, the method of this invention is used to treat a condition selected from baldness, hirsutism, behavioral disorders, spermatogenesis where inhibition of spermatogenesis is desired, psoriasis, Alzheimer's disease, mild cognitive impairment, asthma, type 2 diabetes, optic neuropathy, rheumatoid arthritis, osteoarthritis, major depressive disorder, kidney allografts, oral lichen planus, irritable bowel syndrome (IBS), ulcerative colitis, Crohn's disease, and chemoradiation side effects including but not limited to radiation induced dermatitis and chemotherapy induced mucositis.

Identifying a subject in need of such treatment can be in the judgment of a subject or a health care professional and can be subjective (e.g. opinion) or objective (e.g. measurable by a test or diagnostic method).

In another embodiment, any of the above methods of treatment comprises the further step of co-administering to the subject in need thereof one or more second therapeutic agents. The choice of second therapeutic agent may be made from any second therapeutic agent known to be useful for co-administration with dimethylcurcumin. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I or Ia alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of Formula I or Ia for use in the treatment or prevention in a subject of a disease, disorder or symptom thereof delineated herein.

EXAMPLES

Example 1

Synthesis of (1E,4Z,6E)-1,7-bis(3,4-bis(trideuteromethoxy)phenyl)-5-hydroxyhepta-1,4,6-trien-3-one (Compound 212)

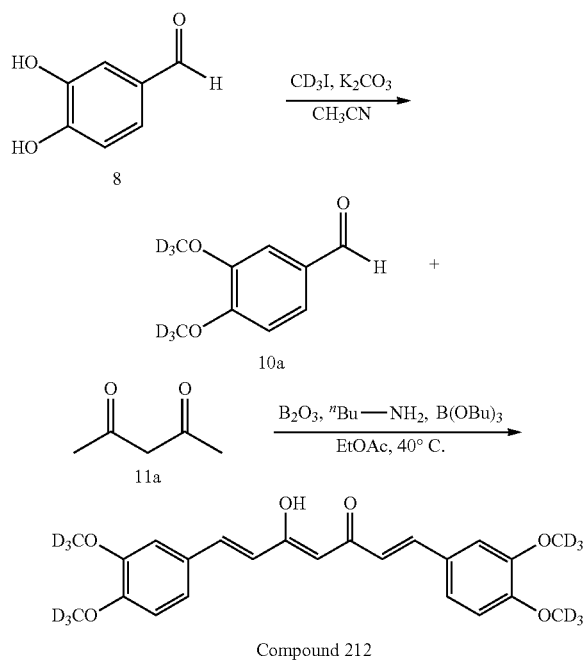

Scheme 4. Synthesis of Compound 212.

Step 1. 3,4-bis(trideuteromethoxy)benzaldehyde (10a): To a suspension of 3,4-dihydroxybenzaldehyde (8, 5.0 g, 36.2 mmol) in acetonitrile (120 mL), was added potassium carbonate (15.0 g, 108.6 mmol). The mixture was stirred vigorously at ambient temperature for 15 minutes. To this reaction mixture was added iodomethane-$d_3$ (7.2 mL, 115.84 mmol; Aldrich, 99.5 atom % D) and then the mixture was heated to 45° C. for a period of 15 hours. The mixture was then cooled to ambient temperature, filtered through Celite®, and concentrated in vacuo. The crude residue was diluted with EtOAc (100 mL) and water (100 mL) and the resulting aqueous layer was further extracted with EtOAc (3×20 mL). The combined organic layers were washed with 10% aqueous $Na_2CO_3$ (2×20 mL), dried ($MgSO_4$), filtered, and concentrated in vacuo to afford aldehyde 10a (5.2 g, 83%). MS (M+H): 173.2.

Step 2. (1E,4Z,6E)-1,7-bis(3,4-bis(trideuteromethoxy)phenyl)-5-hydroxyhepta-1,4,6-trien-3-one (Compound 212): A solution of acetylacetone (11a, 0.29 mL, 2.86 mmol) and boric anhydride (0.14 g, 2.0 mmol) in EtOAc (3 mL) was stirred at 40° C. for a period of 30 min. To this mixture was added tributylborate (1.6 mL, 5.80 mmol) and aldehyde 10a (1.0 g, 5.80 mmol) and the mixture was stirred at 40° C. for a period of 30 min. To the stirred mixture at 40° C. was added dropwise over 15 min a solution of n-butylamine (0.44 mL, 4.4 mmol) in EtOAc (3 mL). The yellow solution was stirred for a period of 24 hours at 40° C. then diluted with 4N HCl (10 mL) at which point the temperature was raised to 60° C. for 30 min. The mixture was then cooled to ambient temperature and diluted with water (15 mL) and EtOAc (15 mL). The mixture was then extracted with EtOAc (3×20 mL) and the combined organic layers washed successively with water and brine. The resulting organic layer was dried ($Na_2SO_4$), filtered, and concentrated in vacuo. The resulting residue was purified by column chromatography ($SiO_2$, 30-50% EtOAc/heptane) to afford Compound 212 as a yellow solid (0.13 g, 16%). $^1$H NMR ($CDCl_3$, 400 MHz): δ 7.60 (d, J=15.6 Hz, 2H), 7.15 (dd, J=8.4, 2.0 Hz, 2H), 7.08 (d, J=1.6 Hz, 2H), 6.88 (d, J=8.4 Hz, 2H), 6.50 (d, J=15.6 Hz, 2H), 5.82 (s, 1H). MS (M+H): 409.3.

Example 2

Synthesis of (1E,4Z,6E)-5-hydroxy-1,7-bis(3-methoxy-4-(trideuteromethoxy)phenyl)hepta-1,4,6-trien-3-one (Compound 214)

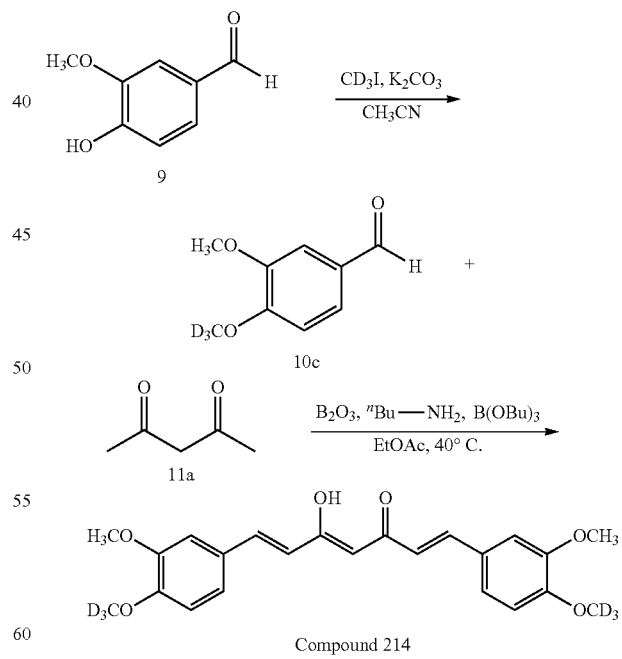

Scheme 5. Synthesis of Compound 214.

Step 1. 3-methoxy-4-(trideuteromethoxy)benzaldehyde (10c): To a suspension of vanillin (9, 5.0 g, 32.9 mmol) in acetonitrile (110 mL), was added potassium carbonate (6.8 g, 49.3 mmol). The mixture was stirred vigorously at ambient temperature for 15 minutes. To this reaction mixture was added iodomethane-d₃ (3.3 mL, 52.6 mmol; Aldrich, 99.5 atom % D) and then the mixture was heated to 45° C. for a period of 15 hours. The mixture was then cooled to ambient temperature, filtered through Celite®, and concentrated in vacuo. The crude residue was diluted with EtOAc (100 mL) and water (100 mL) and the resulting aqueous layer was further extracted with EtOAc (3×20 mL). The combined organic layers were washed with 10% aqueous Na₂CO₃ (2×20 mL), dried (MgSO₄), filtered, and concentrated in vacuo to afford aldehyde 10c (5.0 g, 90%). MS (M+H): 170.2.

Step 2. (1E,4Z,6E)-5-hydroxy-1,7-bis(3-methoxy-4-(trideuteromethoxy)phenyl)hepta-1,4,6-trien-3-one (Compound 214): A solution of acetylacetone (11a, 0.29 mL, 2.86 mmol) and boric anhydride (0.14 g, 2.04 mmol) in EtOAc (3 mL) was stirred at 40° C. for a period of 30 min. To this mixture was added tributylborate (1.6 mL, 5.91 mmol) and aldehyde 10c (1.0 g, 5.91 mmol) and the mixture was stirred at 40° C. for a period of 30 min. To the stirred mixture at 40° C. was added dropwise over 15 min a solution of n-butylamine (0.45 mL, 4.49 mmol) in EtOAc (3 mL). The yellow solution was stirred for a period of 24 hours at 40° C. then diluted with 4N HCl (10 mL) at which point the temperature was raised to 60° C. for 30 min. The mixture was then cooled to ambient temperature and diluted with water (15 mL) and EtOAc (15 mL) followed by filtration through Celite®. The filtrate was extracted with EtOAc (3×20 mL) and the combined organic layers were washed successively with water and brine. The resulting organic layer was dried (Na₂SO₄), filtered, and concentrated in vacuo. The resulting residue was purified by column chromatography (SiO₂, 30-50% EtOAc/heptane) to afford Compound 214 as a yellow solid (0.10 g, 12%). ¹H NMR (CDCl₃, 400 MHz): δ 7.61 (d, J=16.0 Hz, 2H), 7.15 (dd, J=8.4, 2.0 Hz, 2H), 7.08 (d, J=2.0 Hz, 2H), 6.88 (d, J=8.4 Hz, 2H), 6.50 (d, J=15.6 Hz, 2H), 5.82 (s, 1H), 3.94 (s, 6H). MS (M+H): 403.2.

Example 3

Synthesis of (1E,4Z,6E)-1,7-bis(3,4-bis(trideuteromethoxy)phenyl)-1,2,6,7-tetradeutero-5-hydroxyhepta-1,4,6-trien-3-one (Compound 215)

Scheme 6. Synthesis of Compound 215.

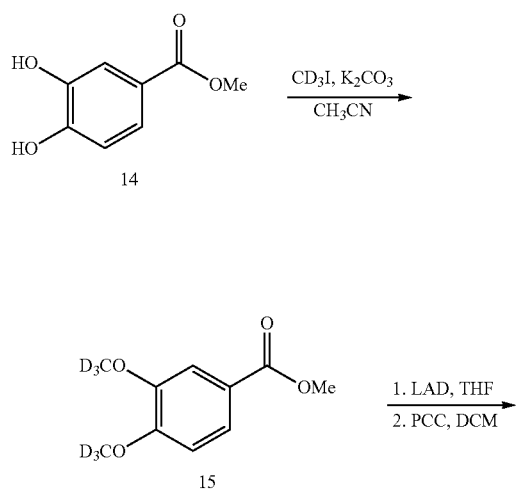

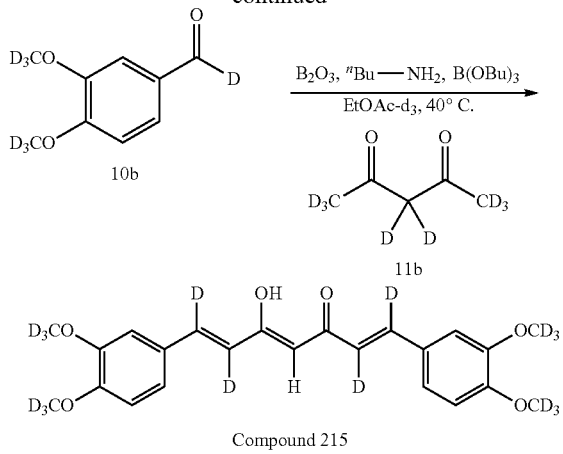

Compound 215

Step 1. Methyl 3,4-bis(trideuteromethoxy)benzoate (15): To a suspension of commercially available methyl 3,4-dihydroxybenzoate (14, 2.0 g, 11.89 mmol) in acetonitrile (50 mL), was added potassium carbonate (4.9 g, 35.67 mmol). The mixture was stirred vigorously at ambient temperature for 15 minutes. To this reaction mixture was added iodomethane-d₃ (2.4 mL, 38.06 mmol; Aldrich, 99.5 atom % D) and then the mixture was heated to 45° C. for a period of 15 hours. The mixture was then cooled to ambient temperature, filtered through Celite®, and concentrated in vacuo. The crude residue was diluted with EtOAc (100 mL) and water (100 mL) and the resulting aqueous layer was further extracted with EtOAc (3×20 mL). The combined organic layers were washed with 10% aqueous Na₂CO₃ (2×20 mL), dried (MgSO₄), filtered, and concentrated in vacuo to afford ester 15 (2.3 g, 97%). MS (M+H): 203.2.

Step 2. 3,4-bis(trideuteromethoxy)benzaldehyde-d₁ (10b): To a solution of ester 15 (2.3 g, 11.49 mmol) in THF (25 mL) at 0° C., was added lithium aluminum deuteride (0.53 g, 12.6 mmol; Cambridge Isotope Labs, 98 atom % D) and the solution was warmed to ambient temperature over a period of 2 hours. To the stirred solution was then added, water (0.53 mL), 15% aqueous NaOH (0.53 mL), and additional water (1.6 mL). The resulting cake was filtered through Celite® and the cake washed with EtOAc (20 mL). The resulting filtrate was concentrated in vacuo to afford the corresponding benzylic alcohol which was used without further purification in the next step.

To a solution of the above benzylic alcohol (2.0 g, 11.34 mmol) in CH₂Cl₂ (40 mL) at 0° C., was added pyridinium chlorochromate (4.1 g, 19.29 mmol) and the solution was warmed to ambient temperature over a period of 2 hours. To the stirred solution was then added heptanes (40 mL) and Celite®. The resulting mixture was stirred at ambient temperature for a period of 1 hour then filtered through a pad of SiO₂ which was washed with CH₂Cl₂. The filtrate was concentrated in vacuo to afford aldehyde 10b (1.4 g, 71%). MS (M+H): 174.3.

Step 3. (1E,4Z,6E)-1,7-bis(3,4-bis(trideuteromethoxy)phenyl)-1,2,6,7-tetradeutero-5-hydroxyhepta-1,4,6-trien-3-one (Compound 215): A suspension of d₈-acetylacetone (11b, 0.43 g, 4.02 mmol, prepared according to the procedure described by Doyle, G. et al., Inorg. Chem. 1968, 7, 2479-2484), and boric anhydride (0.20 g, 2.78 mmol) in EtOAc-d₃ (8 mL) was stirred at 40° C. for a period of 30 min. To this mixture was added tributylborate (2.2 mL, 8.06 mmol) and aldehyde 10b (1.4 g, 8.06 mmol) and the mixture was stirred at 40° C. for a period of 30 min. To the stirred mixture at 40° C. was added dropwise over 15 min a solution of n-butylamine-N,N-d$_2$ (0.62 mL, 6.11 mmol) in EtOAc-d$_3$ (5 mL). The yellow solution was stirred for a period of 24 hours at 40° C. then diluted with 4N HCl (15 mL) at which point the temperature was raised to 60° C. for 30 min. The mixture was then cooled to ambient temperature and diluted with D$_2$O (10 mL) and EtOAc (20 mL) followed by filtration through Celite®. The filtrate was extracted with EtOAc (3×20 mL) and the combined organic layers were washed successively with water and brine. The resulting organic layer was dried (Na$_2$SO$_4$), filtered, and concentrated in vacuo. The resulting residue was purified by column chromatography (SiO$_2$, 30-50% EtOAc/heptane) to afford Compound 215 as a yellow solid (0.17 g, 15%). $^1$H NMR (CDCl$_3$, 400 MHz): δ 7.14 (dd, J=8.4, 2.0 Hz, 2H), 7.07 (d, J=2.0 Hz, 2H), 6.88 (d, J=8.4 Hz, 2H), 5.82 (s, 1H); MS (M+H): 413.4.

Example 4

Synthesis of (1E,4Z,6E)-5-hydroxy-1,7-bis(4-hydroxy-3-(trideuteromethoxy)phenyl)hepta-1,4,6-trien-3-one (Compound 306)

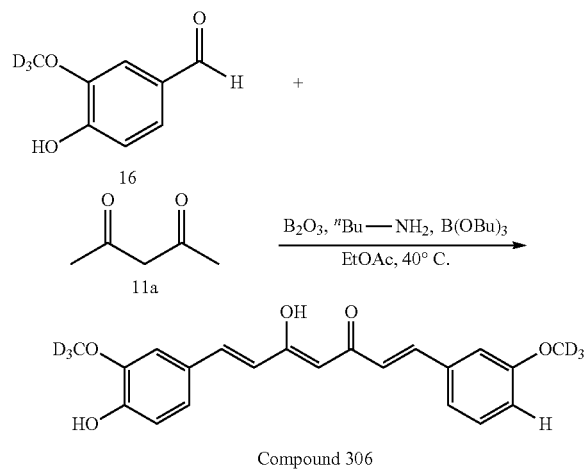

Scheme 7. Synthesis of Compound 306.

(1E,4Z,6E)-5-hydroxy-1,7-bis(4-hydroxy-3-(trideuteromethoxy)phenyl)hepta-1,4,6-trien-3-one (Compound 306): A solution of acetylacetone (11a, 0.32 mL, 3.07 mmol) and boric anhydride (0.15 g, 2.19 mmol) in EtOAc (3 mL) was stirred at 40° C. for a period of 30 min. To this mixture was added tributylborate (1.7 mL, 6.36 mmol) and commercially available 4-hydroxy-3-methoxy-d$_3$ benzaldehyde (1.0 g, 6.36 mmol; Aldrich, 99 atom % D) and the mixture was stirred at 40° C. for a period of 30 min. To the stirred mixture at 40° C. was added dropwise over 15 min a solution of n-butylamine (0.48 mL, 4.82 mmol) in EtOAc (3 mL). The yellow solution was stirred for a period of 24 hours at 40° C. then diluted with 4N HCl (12 mL) at which point the temperature was raised to 60° C. for 30 min. The mixture was then cooled to ambient temperature and diluted with water (15 mL) and EtOAc (15 mL) followed by filtration through Celite®. The filtrate was extracted with EtOAc (3×20 mL) and the combined organic layers were washed successively with water and brine. The resulting organic layer was dried (Na$_2$SO$_4$), filtered, and concentrated in vacuo. The resulting residue was purified by column chromatography (SiO$_2$, 5% MeOH/CHCl$_3$) to afford Compound 306 as a yellow solid (0.109 g, 14%). $^1$H NMR (CDCl$_3$, 400 MHz): δ 9.94 (s, 1H), 7.59 (d, J=16.0 Hz, 2H), 7.12 (d, J=8.0 Hz, 2H), 7.05 (s, 2H), 6.93 (d, J=8.4 Hz, 2H), 6.48 (d, J=16.0 Hz, 2H), 5.86 (br s, 2H), 5.80 (s, 1H). MS (M+H): 373.1.

Example 5

Synthesis of (1E,4Z,6E)-1-(3,4-bis(trideuteromethoxy)phenyl)-5-hydroxy-7-(4-hydroxy-3-(trideuteromethoxy)phenyl)hepta-1,4,6-trien-3-one (Compound 105)

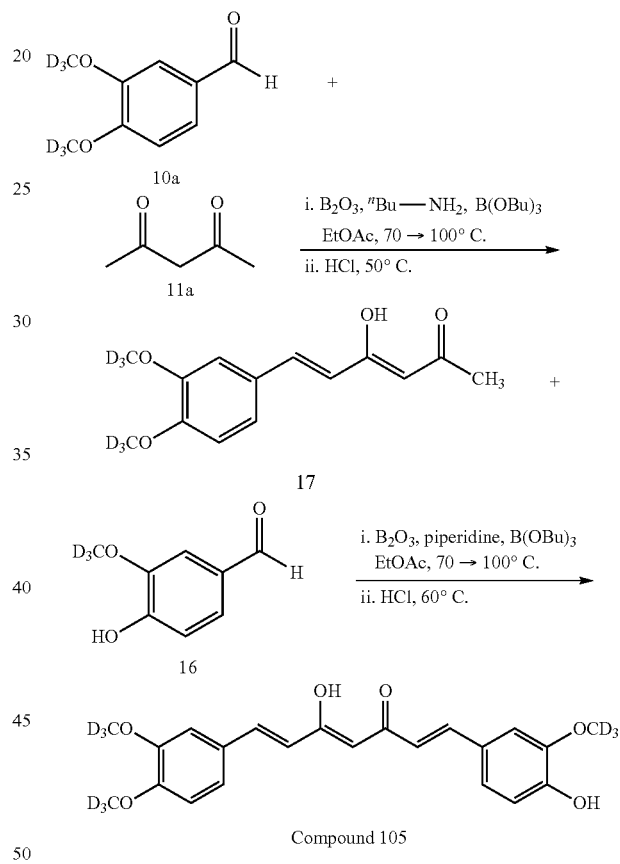

Scheme 8. Synthesis of Compound 105.

Step 1. (3Z,5E)-6-(3,4-bis(trichloromethoxy)phenyl)-4-hydroxyhexa-3,5-dien-2-one (Compound 105): A suspension of acetylacetone (11a, 1.8 mL, 17.42 mmol), and boric anhydride (0.28 g, 4.06 mmol) in EtOAc (8 mL) was stirred at 70° C. for a period of 30 min To this mixture was added tributylborate (1.6 mL, 5.80 mmol) and aldehyde 10a (prepared as described in Example 1; 11.0 g, 5.80 mmol) and the mixture was stirred at 70° C. for a period of 30 min at which point the reaction temperature was increased to 85° C. To the stirred mixture at 85° C., was added dropwise over 15 min a solution of n-butylamine (0.58 mL, 5.80 mmol) in EtOAc (3 mL). The yellow solution was then stirred at 100° C. for a period of 1 hour then cooled to 50° C. and diluted with 1N HCl (15 mL) at which point the mixture was maintained at 50° C. for 30 min. The mixture was then cooled to ambient temperature and diluted with water (20 mL) and EtOAc (20 mL) followed by filtration through Celite®. The filtrate was extracted with EtOAc (3×20 mL) and the combined organic layers were washed successively with water and brine. The resulting organic layer was dried (Na$_2$SO$_4$), filtered and concentrated in vacuo. The resulting residue was purified by column chromatography (SiO$_2$, 10-20% EtOAc/heptane) to afford diene 17 (0.33 g, 22%). MS (M+H): 255.2.

Step 2. (1E,4Z,6E)-1-(3,4-bis(trideuteromethoxy)phenyl)-5-hydroxy-7-(4-hydroxy-3-(trideuteromethoxy)phenyl)hepta-1,4,6-trien-3-one (Compound 105): A suspension of diene 17, (0.33 g, 1.30 mmol), and boric anhydride (63 mg, 0.91 mmol) in EtOAc (3 mL) was stirred at 70° C. for a period of 30 min. To this mixture was added tributylborate (0.70 mL, 2.6 mmol) and commercially available d$_3$-vanillin (16, 0.20 g, 1.30 mmol) and the mixture was stirred at 70° C. for a period of 30 min at which point the reaction temperature was increased to 85° C. To the stirred mixture at 85° C. was added dropwise over 15 min a solution of piperidine (0.13 mL, 1.30 mmol) in EtOAc (2 mL). The yellow solution was then stirred at 100° C. for a period of 1 hour then cooled to 60° C. and diluted with 1N HCl (15 mL) at which point the mixture was maintained at 60° C. for 30 min. The mixture was then cooled to ambient temperature and diluted with water (20 mL) and EtOAc (20 mL) followed by filtration through Celite®. The filtrate was extracted with EtOAc (3×20 mL) and the combined organic layers were washed successively with water and brine. The resulting organic layer was dried (Na$_2$SO$_4$), filtered, and concentrated in vacuo. The resulting residue was purified by column chromatography (SiO$_2$, 30-50% EtOAc/heptane) to afford Compound 105 as a yellow solid (0.10 g, 20%). $^1$H NMR (CDCl$_3$, 400 MHz): δ 16.05 (br s, 1H), 7.60 (dd, J=16.0, 5.6 Hz, 2H), 7.13 (dt, J=8.4, 2.0 Hz, 2H), 7.06 (dd, J=11.6, 1.6 Hz, 2H), 6.90 (dd, J=23.2, 8.4 Hz, 2H), 6.49 (dd, J=15.6, 6.0 Hz, 2H), 5.81 (s, 1H). MS (M+H): 392.2.

Example 6

Synthesis of (1E,4Z,6E)-1,2,6,7-tetradeutero-5-hydroxy-1,7-bis(4-hydroxy-3-(trideuteromethoxy)phenyl)hepta-1,4,6-trien-3-one (Compound 307)

Scheme 9. Synthesis of Compound 307.

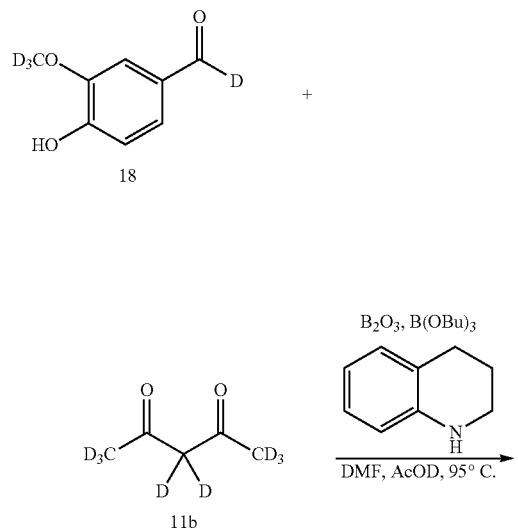

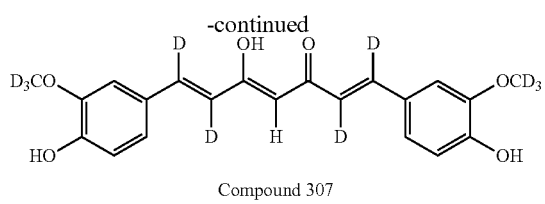

Compound 307

(1E,4Z,6E)-1,2,6,7-tetradeutero-5-hydroxy-1,7-bis(4-hydroxy-3-(trideuteromethoxy)phenyl)hepta-1,4,6-trien-3-one (Compound 307): A suspension of 11b (0.19 g, 1.76 mmol, prepared according to the procedure described by Doyle, G. et al., Inorg. Chem. 1968, 7, 2479-2484), boric anhydride (0.12 g, 1.76 mmol), and tributylborate (0.95 mL, 3.52 mmol) in DMF (2 mL) was stirred at 65° C. for a period of 15 min. To this reaction mixture was added d$_4$-vanillin (18, 0.55 g, 3.52 mmol) and the mixture was stirred at 65° C. for a period of 10 min. To the stirred mixture at 65° C., was added a solution of 1,2,3,4-tetrahydroquinoline (0.05 mL) and AcOD (0.11 mL) in DMF (1 mL). The yellow solution was then heated to 95° C. for a period of 4 hours then cooled to ambient temperature and diluted with 20% AcOD/D$_2$O (10 mL) at which point the temperature was raised to 70° C. for 1 hour. The mixture was then cooled to ambient temperature and concentrated in vacuo. The crude residue was diluted with EtOAc (100 mL) and water (100 mL) and the resulting aqueous layer was further extracted with EtOAc (3×20 mL). The combined organic layers were dried (Na$_2$SO$_4$), filtered, and concentrated in vacuo. The resulting residue was purified by column chromatography (SiO$_2$, 30-50% EtOAc/heptane) to afford Compound 307 as a yellow solid (0.26 g, 39%). $^1$H NMR (CDCl$_3$, 400 MHz) δ 16.0 (br s, 1H), 7.12 (dd, J=8.4, 2.0 Hz, 2H), 7.04 (d, J=1.6 Hz, 2H), 6.94 (d, J=8.0 Hz, 2H), 5.86 (br s, 2H), 5.80 (s, 1H). MS (M+H): 379.1.

Example X

Evaluation of Metabolic Stability

Microsomal Assay: Human liver microsomes (20 mg/mL) are obtained from Xenotech, LLC (Lenexa, Kans.). β-nicotinamide adenine dinucleotide phosphate, reduced form (NADPH), magnesium chloride (MgCl$_2$), and dimethyl sulfoxide (DMSO) are purchased from Sigma-Aldrich.

Determination of Metabolic Stability: 7.5 mM stock solutions of test compounds are prepared in DMSO. The 7.5 mM stock solutions are diluted to 12.5-50 μM in acetonitrile (ACN). The 20 mg/mL human liver microsomes are diluted to 0.625 mg/mL in 0.1 M potassium phosphate buffer, pH 7.4, containing 3 mM MgCl$_2$. The diluted microsomes are added to wells of a 96-well deep-well polypropylene plate in triplicate. A 10 μL aliquot of the 12.5-50 μM test compound is added to the microsomes and the mixture is pre-warmed for 10 minutes. Reactions are initiated by addition of pre-warmed NADPH solution. The final reaction volume is 0.5 mL and contains 0.5 mg/mL human liver microsomes, 0.25-1.0 μM test compound, and 2 mM NADPH in 0.1 M potassium phosphate buffer, pH 7.4, and 3 mM MgCl$_2$. The reaction mixtures are incubated at 37° C., and 50 μL aliquots are removed at 0, 5, 10, 20, and 30 minutes and added to shallow-well 96-well plates which contain 50 μL of ice-cold ACN with internal standard to stop the reactions. The plates are stored at 4° C. for 20 minutes after which 100 μL of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer.

The same procedure is followed for the non-deuterated counterpart of the compound of Formula I and the positive control, 7-ethoxycoumarin (1 μM). Testing is done in triplicate.

Data analysis: The in vitro $t_{1/2}$s for test compounds are calculated from the slopes of the linear regression of % parent remaining (ln) vs incubation time relationship.

in vitro $t_{1/2}$=0.693/k k=−[slope of linear regression of % parent remaining(ln) vs incubation time]

Data analysis is performed using Microsoft Excel Software.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

We claim:

1. A compound of Formula I:

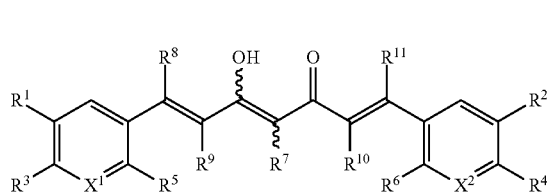

I or a pharmaceutically acceptable salt thereof or a tautomer thereof, wherein:
$R^1$, $R^2$, $R^3$ and $R^4$ are each independently selected from the group consisting of —OH, —O($C_1$-$C_6$ alkyl), —$NO_2$, —$NH_2$, —NH($C_1$-$C_6$ alkyl) and —N($C_1$-$C_6$ alkyl)$_2$, wherein each $C_1$-$C_6$ alkyl is optionally and independently substituted with one or more deuterium;

$R^5$ and $R^6$ are each independently hydrogen, deuterium, halo, or —$NO_2$;

$R^7$ is hydrogen, deuterium, or —$R^{13}$;

$R^{13}$ is ($C_2$-$C_6$) alkenyl optionally substituted with one or more deuterium and substituted with —C(O)$R^{12}$;

$R^{12}$ is —$OCH_3$, —$OCH_2CH_3$, —NH($CH_2CH_3$), —CN, or —$CH_2OH$, wherein each of —$OCH_3$, —$OCH_2CH_3$, —NH($CH_2CH_3$), and —$CH_2OH$ is optionally substituted with one or more deuterium;

$R^8$ and $R^{11}$ are each independently hydrogen or deuterium;

$R^9$ and $R^{10}$ are each independently hydrogen or deuterium;

$X^1$ and $X^2$ are each independently CH, CD, C($OCH_3$), C($OCD_3$) or C($NO_2$);

provided that at least one of $R^1$, $R^2$, $R^3$, $R^4$, $R^5$, $R^6$, $R^7$, $R^8$, $R^{11}$, $R^9$, $R^{10}$, $X^1$ and $X^2$ comprises deuterium;

and provided that the compound of Formula I is not

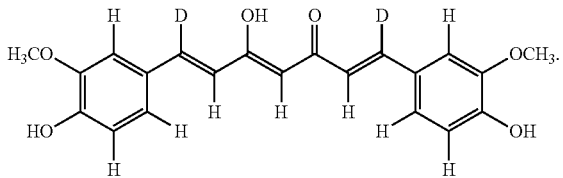 [SMILES: [2H]/C(=C\C(=O)/C=C(O)/C=C(\[2H])c1ccc(O)c(OC)c1)c1ccc(O)c(OC)c1]

2. The compound of claim 1, wherein $R^1$, $R^2$, $R^3$, and $R^4$ are independently selected from —OH, —$OCH_3$, and —$OCD_3$.

3. The compound of claim 1, wherein $R^5$ and $R^6$ are each hydrogen or each deuterium.

4. The compound of claim 1, wherein $R^7$ is hydrogen or deuterium.

5. The compound of claim 1, wherein $X^1$ is CH or CD.

6. The compound of claim 1, wherein $X^2$ is CH or CD.

7. The compound of claim 1, wherein $R^7$ is $R^{13}$, wherein $R^{13}$ is ($C_2$-$C_6$) alkenyl optionally substituted with one or more deuterium and with —C(O)$R^{12}$, and $R^{12}$ is —$OCD_3$, —$OCD_2CD_3$, —N(H)$CD_2CD_3$, or —$CD_2OH$.

8. The compound of claim 1 wherein $X^1$=$X^2$=CH, $R^5$=$R^6$=H and wherein the compound is any one of the compounds of the following table, wherein any atom not designated as deuterium is present at its natural isotopic abundance:

| Compound | $R^1$ | $R^2$ | $R^3$ | $R^4$ | $R^7$ | $R^8$ | $R^9$ | $R^{10}$ | $R^{11}$ |
|---|---|---|---|---|---|---|---|---|---|
| 100 | $OCD_3$ | $OCD_3$ | OH | $OCD_3$ | D | D | D | D | D |
| 101 | $OCD_3$ | $OCD_3$ | OH | $OCD_3$ | H | D | D | D | D |
| 102 | $OCD_3$ | $OCD_3$ | OH | $OCD_3$ | H | H | D | D | D |
| 103 | $OCD_3$ | $OCD_3$ | OH | $OCD_3$ | H | D | D | D | H |
| 104 | $OCD_3$ | $OCD_3$ | OH | $OCD_3$ | H | H | D | D | H |
| 105 | $OCD_3$ | $OCD_3$ | OH | $OCD_3$ | H | H | H | H | H |
| 106 | $OCD_3$ | $OCD_3$ | OH | $OCD_3$ | H | D | H | H | D |
| 107 | $OCD_3$ | $OCD_3$ | OH | $OCD_3$ | H | D | H | H | H |
| 108 | $OCD_3$ | $OCD_3$ | OH | $OCD_3$ | H | H | H | H | D |
| 109 | $OCH_3$ | $OCD_3$ | OH | $OCD_3$ | D | D | D | D | D |
| 110 | $OCH_3$ | $OCD_3$ | OH | $OCD_3$ | H | D | D | D | D |
| 111 | $OCH_3$ | $OCD_3$ | OH | $OCD_3$ | H | H | D | D | D |
| 112 | $OCH_3$ | $OCD_3$ | OH | $OCD_3$ | H | D | D | D | H |
| 113 | $OCH_3$ | $OCD_3$ | OH | $OCD_3$ | H | H | D | D | H |
| 114 | $OCH_3$ | $OCD_3$ | OH | $OCD_3$ | H | H | H | H | H |
| 115 | $OCH_3$ | $OCD_3$ | OH | $OCD_3$ | H | D | H | H | D |
| 116 | $OCH_3$ | $OCD_3$ | OH | $OCD_3$ | H | D | H | H | H |
| 117 | $OCH_3$ | $OCD_3$ | OH | $OCD_3$ | H | H | H | H | D |
| 118 | $OCD_3$ | $OCH_3$ | OH | $OCH_3$ | D | D | D | D | D |
| 119 | $OCD_3$ | $OCH_3$ | OH | $OCH_3$ | H | D | D | D | D |
| 120 | $OCD_3$ | $OCH_3$ | OH | $OCH_3$ | H | H | D | D | D |
| 121 | $OCD_3$ | $OCH_3$ | OH | $OCH_3$ | H | D | D | D | H |
| 122 | $OCD_3$ | $OCH_3$ | OH | $OCH_3$ | H | H | D | D | H |
| 123 | $OCD_3$ | $OCH_3$ | OH | $OCH_3$ | H | H | H | H | H |
| 124 | $OCD_3$ | $OCH_3$ | OH | $OCH_3$ | H | D | H | H | D |
| 125 | $OCD_3$ | $OCH_3$ | OH | $OCH_3$ | H | D | H | H | H |
| 126 | $OCD_3$ | $OCH_3$ | OH | $OCH_3$ | H | H | H | H | D |
| 127 | $OCH_3$ | $OCH_3$ | OH | $OCH_3$ | D | D | D | D | D |
| 128 | $OCH_3$ | $OCH_3$ | OH | $OCH_3$ | H | D | D | D | D |
| 129 | $OCH_3$ | $OCH_3$ | OH | $OCH_3$ | H | H | D | D | D |
| 130 | $OCH_3$ | $OCH_3$ | OH | $OCH_3$ | H | D | D | D | H |
| 131 | $OCH_3$ | $OCH_3$ | OH | $OCH_3$ | H | H | D | D | H |
| 132 | $OCH_3$ | $OCH_3$ | OH | $OCH_3$ | H | D | H | H | D |
| 133 | $OCH_3$ | $OCH_3$ | OH | $OCH_3$ | H | D | H | H | H |
| 134 | $OCH_3$ | $OCH_3$ | OH | $OCH_3$ | H | H | H | H | D | or a pharmaceutically acceptable salt thereof or a tautomer thereof.

9. The compound of claim 1, wherein the compound of Formula I is a compound of Formula Ia:

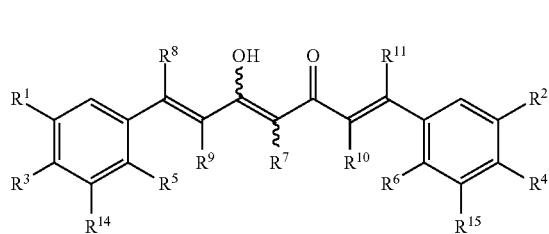

(Ia)

or a pharmaceutically acceptable salt thereof or a tautomer thereof, wherein:
- $R^1$ and $R^2$ are the same and are selected from the group consisting of —OH, —O($C_1$-$C_6$ alkyl), —$NO_2$, —$NH_2$, —NH($C_1$-$C_6$ alkyl) and —N($C_1$-$C_6$ alkyl)$_2$, wherein each $C_1$-$C_6$ alkyl is optionally and independently substituted with one or more deuterium;
- $R^3$ and $R^4$ are the same and are selected from the group consisting of —OH, —O($C_1$-$C_6$ alkyl), —$NO_2$, —$NH_2$, —NH($C_1$-$C_6$ alkyl) and —N($C_1$-$C_6$ alkyl)$_2$, wherein each $C_1$-$C_6$ alkyl is optionally and independently substituted with one or more deuterium;
- $R^5$ and $R^6$ are the same and are selected from the group consisting of hydrogen and deuterium;
- $R^7$ is selected from hydrogen and deuterium;
- $R^9$ and $R^{10}$ are the same and are selected from hydrogen and deuterium;
- $R^8$ and $R^{11}$ are the same and are selected from hydrogen and deuterium;
- $R^{14}$ and $R^{15}$ are the same and are selected from hydrogen and deuterium;
- provided that at least one of $R^1$, $R^2$, $R^3$, $R^4$, $R^5$, $R^6$, $R^7$, $R^8$, $R^{11}$, $R^9$, $R^{10}$, $R^{14}$ and $R^{15}$ comprises deuterium;
- and provided that the compound of Formula Ia is not

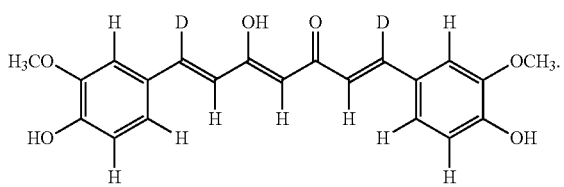 [SMILES: [2H]/C(=C\C(=O)/C=C(O)/C=C(\[2H])c1ccc(O)c(OC)c1)c1ccc(O)c(OC)c1]

10. The compound of claim 9, wherein $R^1$ and $R^2$ are the same and are selected from —OH, —$OCH_3$ and —$OCD_3$; and $R^3$ and $R^4$ are the same and are selected from —OH, —$OCH_3$ and —$OCD_3$.

11. The compound of claim 10, wherein $R^1$ and $R^2$ are the same and are selected from —$OCH_3$ and —$OCD_3$; and $R^3$ and $R^4$ are both —OH.

12. The compound of claim 9, wherein $R^7$, $R^9$ and $R^{10}$ are the same and are selected from hydrogen and deuterium.

13. The compound of claim 1, wherein any atom not designated as deuterium is present at its natural isotopic abundance.

14. The compound of claim 9, wherein $R^5$=$R^6$=H, and $R^{14}$=$R^{15}$=H, and wherein the compound is any one of the compounds of the following table, wherein any atom not designated as deuterium is present at its natural isotopic abundance:

| Compound | $R^1$=$R^2$ | $R^3$=$R^4$ | $R^7$ | $R^8$=$R^{11}$ | $R^9$=$R^{10}$ |
|---|---|---|---|---|---|
| 200 | $OCD_3$ | $OCD_3$ | D | D | D |
| 201 | $OCD_3$ | $OCH_3$ | D | D | D |
| 202 | $OCH_3$ | $OCD_3$ | D | D | D |
| 203 | $OCH_3$ | $OCH_3$ | D | D | D |
| 204 | $OCD_3$ | $OCD_3$ | D | H | D |
| 205 | $OCD_3$ | $OCD_3$ | H | D | H |
| 206 | $OCD_3$ | $OCH_3$ | D | H | D |
| 207 | $OCD_3$ | $OCH_3$ | H | D | H |
| 208 | $OCH_3$ | $OCD_3$ | D | H | D |
| 209 | $OCH_3$ | $OCD_3$ | H | D | H |
| 210 | $OCH_3$ | $OCH_3$ | D | H | D |
| 211 | $OCH_3$ | $OCH_3$ | H | D | H |
| 212 | $OCD_3$ | $OCD_3$ | H | H | H |
| 213 | $OCD_3$ | $OCH_3$ | H | H | H |
| 214 | $OCH_3$ | $OCD_3$ | H | H | H |
| 215 | $OCD_3$ | $OCD_3$ | H | D | D |
| 216 | $OCD_3$ | $OCH_3$ | H | D | D |
| 217 | $OCH_3$ | $OCD_3$ | H | D | D |
| 218 | $OCH_3$ | $OCH_3$ | H | D | D |
| 219 | $OCD_3$ | $OCD_3$ | H | H | D |
| 220 | $OCD_3$ | $OCH_3$ | H | H | D |
| 221 | $OCH_3$ | $OCD_3$ | H | H | D |
| 222 | $OCH_3$ | $OCH_3$ | H | H | D | or a pharmaceutically acceptable salt thereof or tautomer thereof.

15. The compound of claim 9, wherein $R^5$=$R^6$=H, and $R^{14}$=$R^{15}$=H, and wherein the compound is any one of the compounds of the following table, wherein any atom not designated as deuterium is present at its natural isotopic abundance:

| Compound | $R^1$=$R^2$ | $R^3$=$R^4$ | $R^7$ | $R^8$=$R^{11}$ | $R^9$=$R^{10}$ |
|---|---|---|---|---|---|
| 300 | $OCD_3$ | OH | D | D | D |
| 301 | $OCH_3$ | OH | D | D | D |
| 302 | $OCD_3$ | OH | D | H | D |
| 303 | $OCD_3$ | OH | H | D | H |
| 304 | $OCH_3$ | OH | D | H | D |
| 306 | $OCD_3$ | OH | H | H | H |
| 307 | $OCD_3$ | OH | H | D | D |
| 308 | $OCH_3$ | OH | H | D | D |
| 309 | $OCD_3$ | OH | H | H | D |
| 310 | $OCH_3$ | OH | H | H | D | or a pharmaceutically acceptable salt thereof or tautomer thereof.

16. A pyrogen-free pharmaceutical composition comprising an effective amount of the compound of claim 1, or a pharmaceutically acceptable salt thereof or tautomer thereof; and a pharmaceutically acceptable carrier.

17. A method of treating a disease selected from the group consisting of baldness, hirsutism, behavioral disorders, acne, alopecia, skin lesions, Kennedy's disease or spinobulbar muscular atrophy and spermatogenesis where inhibition of spermatogenesis is desired, psoriasis, Alzheimer's disease, mild cognitive impairment, asthma, type 2 diabetes, optic neuropathy, rheumatoid arthritis, osteoarthritis, major depressive disorder, kidney allografts, oral lichen planus, irritable bowel syndrome (IBS), ulcerative colitis, Crohn's disease, chemoradiation side effects, multiple myeloma, pancreatic cancer, myleodysplastic syndromes, colon cancer, colorectal cancer, skin cancer, small cell lung cancer, testicular cancer, lymphoma, leukemia, esophageal cancer, stomach cancer, breast cancer, endometrial cancer, ovarian cancer, central nervous system cancer, liver cancer, prostate cancer, familial adenomatous polyposis (FAP), uterine cervical dysplasia, cutaneous T-cell lymphoma, head and neck cancer and osteosarcoma comprising the step of administering to the subject an effective amount of a compound of claim 1 or a pharmaceutically acceptable salt thereof or tautomer thereof.

18. The method of claim 17 wherein the disease is selected from multiple myeloma, pancreatic cancer, myleodysplastic syndromes, colon cancer, colorectal cancer, skin cancer, small cell lung cancer, testicular cancer, lymphoma, leukemia, esophageal cancer, stomach cancer, breast cancer, endometrial cancer, ovarian cancer, central nervous system cancer, liver cancer, prostate cancer, familial adenomatous polyposis (FAP), uterine cervical dysplasia, cutaneous T-cell lymphoma, head and neck cancer and osteosarcoma.

\* \* \* \* \*